United States Patent [19]
Yoo

[11] Patent Number: 5,487,883
[45] Date of Patent: Jan. 30, 1996

[54] PROCESS FOR PRODUCING MOXAS

[76] Inventor: Tae W. Yoo, 807, 1-Dong, Hanyang, Apt. 32-5, Banpo-dong, Seocho-ku, Seoul, Rep. of Korea

[21] Appl. No.: 319,962

[22] Filed: Oct. 7, 1994

[30] Foreign Application Priority Data

Dec. 8, 1993 [KR] Rep. of Korea .................. 93-26782

[51] Int. Cl.⁶ .................. A01N 25/06; A01N 25/18; A01N 25/20
[52] U.S. Cl. .................................................. 424/40
[58] Field of Search .................................. 424/40

[56] References Cited

U.S. PATENT DOCUMENTS

| | | | |
|---|---|---|---|
| 215,945 | 5/1879 | Lindesmith | 424/40 |
| 1,216,710 | 2/1917 | Lucas | 424/40 |
| 1,519,053 | 12/1924 | Rew | 424/40 |

*Primary Examiner*—Nathan M. Nutter
*Attorney, Agent, or Firm*—Richard M. Goldberg

[57] ABSTRACT

A process for producing moxas comprises mixing 90 weight % of the carbonized wormwood powder, 3–7 weight % of ceramic powder and 3–7 weight % of the powder of Sabina Chinensis. The moxibusting implement of this invention is superior in fomentation effect and thermal efficiency by far infrared rays radiating from the ceramic powder, and it is effective in enhancing intensity of the moxibusting implement by the ceramic powder, and in deodorizing by the powder of ceramic and Sabina Chinensis.

18 Claims, No Drawings

PROCESS FOR PRODUCING MOXAS

BACKGROUND OF THE INVENTION

1. Field of the Invention

The present invention relates to a process for producing moxas. More particularly, it relates to a process for producing moxas by carbonizing a wormwood which is used as a plant for food or a Chinese medicine, and then by mixing it with the powder of Sabina Chinensis and ceramic powder(Korean patent publication No. 93-3: weight ratio; $SiO_2$ 75–40%, $Fe_2O_3$ 1.5–0.2%, $Al_2O_3$ 5–38%, C 4–7.7%, MgO 1–12.7%, CaO 0.4–2.0%, $K_2O$ 0.1–0.5%, FeO 0.1–0.5%, $Na_2O$ 0.5–2.0%, $TiO_2$ 0.1–0.5%, BeO 2–4%) under conditions of stirring and heating.

2. Description of the Prior Art

In Chinese medicine, a wormwood has been traditionally used to treat diseases. When it is burned at Meridian Points on the skin, a treatment effect can be obtained. However, although this method is convenient to use because of the use of the solid fixed size, there is a problem that the treatment effect fails.

As another example, them is the method of using a moxibusting implement produced by shattering the dried wormwood material, followed by wrapping it up in thin paper as is done with tobacco, by cutting it in a fixed length, and then by securing it on a round thick paper board having a receiving hole at the center thereof, the latter step being an improvement on the above method. When the moxibusting implement is burned at Meridian Points on the skin, a treatment effect can be obtained by bringing heat into contact with the skin through the receiving hole.

However, this method also has a problem that harmful smoke occurs during burning because the moxibusting implement is wrapped in thin paper in the form of a bar. Thus, in the case of cauterizing with moxas at many Meridian Points on the skin, so much smoke occurs that a third person as well as a user feel unpleasant.

In the above two cases, because a Turpentine Oil which is included in wormwood ingredients, namely wormwood resin, is not eliminated, bad smell and smoke occur during burning of moxas.

Accordingly, in the extreme case, a disease may attack a respiratory organ and a sight problem may arise.

SUMMARY OF THE INVENTION

The object of the present invention is to provide a process for producing moxas which can overcome the problems described above. Thus, the present invention functions to increase the fomentation effect and thermal efficiency by far infrared rays radiating from the ceramic powder, to deodorize by the ceramic powder and Sabina Chinensis, and further to enhance the intensity of the moxibusting implement by the ceramic powder.

According to the invention, to accomplish the above object, there is provided a process for producing moxas which comprises mixing 90 weight % of the carbonized wormwood powder prepared by shattering wormwood to such an extent that it passes through a 300 to 330 mesh screen and carbonizing the powder, 3–7 weight % of ceramic powder (Korean patent publication No. 93-3) and 3–7 weight % of the powder of Sabina Chinensis.

The objects of the present invention will be hereinafter explained in detail with reference to the processes for production.

DESCRIPTION OF PREFERRED EMBODIMENTS

PROCESS 1

The dried wormwood was shattered to such an extent that it passed through 300–330 mesh screen.

PROCESS 2

The shattered wormwood obtained in Process 1 described above was sealed up in a crucible at high temperature.

PROCESS 3

The crucible described above was put in an oven, heated in the range of temperature of 500° to 700° C. for 2 hours to obtain a carbonized wormwood powder,

PROCESS 4

About 90 weight % of the carbonized wormwood powder prepared in Process 3 described above was added to 3–7 weight 94 of the powder of Sabina Chinensis, preferably of 4–6 weight %, and more preferably about 5 weight %, and 3–7 weight % ceramic powder, preferably 4–6 weight %, and more preferably about 5 weight %.

Further, a small amount of starch was added to the above mixture to enhance its viscosity at the time of making in the form of a bar.

PROCESS 5

The product prepared in Process 1 described above was made into a moxibusting implement by machine (not shown).

To summarize the advantages obtained by the invention, the intensity of the moxibusting implement is enhanced by adding the ceramic powder and because far infrared rays radiating from the ceramic powder are useful in increasing the fomentation effect and thermal efficiency, the effect of moxacautery can be doubled. Further, by adding the powder of ceramic and Sabina Chinensis, deodorization can be obtained. Thus, the moxibusting implement of this invention does not have a bad smell. Because of the use of the carbonized wormwood powder and the disuse of the thin paper to wrap the moxibusting implement, the amount of smoke is decreased. The moxibusting implement of this invention can be used widely without regard to the place and the mount used.

What is claimed is:

1. A process for producing moxas comprising the step of mixing 90 weight % of carbonized wormwood powder with 3–7 weight % of ceramic powder and 3–7 weight % of powder of Sabina Chinensis.

2. A process for producing moxas comprising the steps of:

preparing carbonized wormwood powder by shattering wormwood to such an extent that it passes through a 300–330 mesh screen, thereafter sealing up said prepared wormwood powder in a crucible, then heating said sealed powder in an oven, and then mixing 90 weight % of said heated carbonized wormwood powder with 3–7 weight % of ceramic powder and 3–7 weight % of powder of Sabina Chinensis.

3. The process according to claim 2, wherein the temperature of heating is in the range from 500° to 700° C.

4. The process according to claim 1, wherein said ceramic powder has the following composition and weight ratios: $SiO_2$ (75–40%), $Fe_2O_3$ (1.5–0.2%), $Al_2O_3$ (5–38%), C (4–7.7%), MgO (1–12.7%), CaO (0.4–2.0%), $K_2O$ (0.1–0.5%), FeO (0.1–0.5%), $Na_2O$ (0.5–2.0%), $TiO_2$ (0.1–0.5%) and BeO (2–4%).

5. The process according to claim 3, wherein said step of heating occurs for a period of approximately two hours.

6. The process according to claim 1, wherein said ceramic powder has a 4–6 weight % in said step of mixing.

7. The process according to claim 6, wherein said ceramic powder has a 5 weight % in said step of mixing.

8. The process according to claim 1, wherein said powder of Sabina Chinensis has a 4–6 weight % in said step of mixing.

9. The process according to claim 8, wherein said power of Sabina Chinensis has a 5 weight % in said step of mixing.

10. The process according to claim 1, further comprising the step of adding starch to said mixture, after said step of mixing.

11. A moxa comprising a mixture of:

90 weight % of carbonized wormwood powder;

3–7 weight % of ceramic powder; and

3–7 weight % of powder of Sabina Chinensis.

12. A moxa according to claim 11, wherein said carbonized wormwood powder has a particle size that will pass through a 300–330 mesh screen.

13. A moxa according to claim 11, wherein said ceramic powder has the following composition and weight ratios: $SiO_2$ (75–40%), $Fe_2O_3$ (1.5–0.2%), $Al_2O_3$ (5–38%), C (4–7.7%), MgO (1–12.7%), CaO (0.4–2.0%), $K_2O$ (0.1–0.5%), FeO (0.1–0.5%), $Na_2O$ (0.5–2.0%), $TiO_2$ (0.1–0.5%) and BeO (2–4%).

14. A moxa according to claim 11, wherein said ceramic powder has a 4–6 weight %.

15. A moxa according to claim 14, wherein said ceramic powder has a 5 weight %.

16. A moxa according to claim 11, wherein said powder of Sabina Chinensis has a 4–6 weight %.

17. A moxa according to claim 16, wherein said power of Sabina Chinensis has a 5 weight %.

18. A moxa according to claim 11, wherein said mixture further includes starch.

* * * * *

UNITED STATES PATENT AND TRADEMARK OFFICE
CERTIFICATE OF CORRECTION

PATENT NO. : 5,487,883
DATED : JANUARY 30, 1996
INVENTOR(S) : TAE WOO YOO

It is certified that error appears in the above-indentified patent and that said Letters Patent is hereby corrected as shown below:

Column 2, line 22, after "powder" change "," to --.-- line 28, change "94" to --%-- line 38, change "1" to --4-- line 54, change "mount" to --amount--

Signed and Sealed this

Twenty-third Day of April, 1996

BRUCE LEHMAN

Attest:

Attesting Officer

Commissioner of Patents and Trademarks